(12) United States Patent
Flint et al.

(10) Patent No.: US 12,161,884 B2
(45) Date of Patent: Dec. 10, 2024

(54) METHODS FOR USE WITH A COMPONENT OF A BEAM LIMITING DEVICE

(71) Applicant: Elekta Limited, Crawley (GB)

(72) Inventors: Chris Flint, Crawley (GB); German Vega, Crawley (GB); Keith Richardson, Crawley (GB); Alessandra Chiap, Crawley (GB)

(73) Assignee: Elekta Limited, Crawley (GB)

( * ) Notice: Subject to any disclaimer, the term of this patent is extended or adjusted under 35 U.S.C. 154(b) by 280 days.

(21) Appl. No.: 17/597,485

(22) PCT Filed: Jul. 9, 2020

(86) PCT No.: PCT/EP2020/069465
§ 371 (c)(1),
(2) Date: Jan. 7, 2022

(87) PCT Pub. No.: WO2021/005188
PCT Pub. Date: Jan. 14, 2021

(65) Prior Publication Data
US 2022/0280813 A1    Sep. 8, 2022

(30) Foreign Application Priority Data
Jul. 9, 2019    (GB) ..................... 1909848

(51) Int. Cl.
*A61N 5/10* (2006.01)
*G21K 1/04* (2006.01)
(52) U.S. Cl.
CPC ......... *A61N 5/1045* (2013.01); *A61N 5/1048* (2013.01); *G21K 1/046* (2013.01)
(58) Field of Classification Search
CPC .... A61N 5/1045; A61N 5/1048; G21K 1/046; G06Q 10/04
See application file for complete search history.

(56) References Cited

U.S. PATENT DOCUMENTS

2014/0239204 A1   8/2014   Orton et al.
2014/0320019 A1   10/2014  Smith
(Continued)

FOREIGN PATENT DOCUMENTS

CN   107272659 A  * 10/2017  ......... G05B 23/0213
CN   104689490 B    12/2017
(Continued)

OTHER PUBLICATIONS

"United Kingdom Application Serial No. 2111375.8 Examination Report dated Mar. 9, 2022", (Mar. 9, 2022), 6 pgs.
(Continued)

*Primary Examiner* — Christine S. Kim
(74) *Attorney, Agent, or Firm* — Schwegman Lundberg & Woessner, P.A.

(57) ABSTRACT

Disclosed herein is a method of determining whether repair or replacement of a multi-leaf collimator for a radiotherapy device should be scheduled. The multi-leaf collimator comprises a leaf bank comprising a plurality of leaves, a leaf bank support configured to support the leaf bank, a leaf bank guide, and a guide actuation means configured to extend the leaf bank along the leaf bank guide into the path of a radiation beam. The device further comprises current sensing means configured to produce a signal indicative of the current supplied to the guide actuation means. The method comprises receiving signals from the current sensing means; processing the signals; and based on the processing, determining whether repair or replacement of the multi-leaf collimator should be scheduled.

19 Claims, 11 Drawing Sheets

(56) References Cited

U.S. PATENT DOCUMENTS

| | | |
|---|---|---|
| 2014/0341351 A1 | 11/2014 | Berwick et al. |
| 2019/0175944 A1 | 6/2019 | Towe et al. |
| 2021/0247248 A1 | 8/2021 | Kobayashi |

FOREIGN PATENT DOCUMENTS

| | | |
|---|---|---|
| CN | 108211134 A | 6/2018 |
| EP | 2085117 | 8/2009 |
| EP | 3088047 | 11/2016 |
| JP | 3703060 B2 | 7/2005 |
| WO | 2011107111 | 9/2011 |

OTHER PUBLICATIONS

"International Application Serial No. PCT/EP2020/069465, International Search Report dated Aug. 28, 2020", (Aug. 28, 2020), 3 pgs.

"International Application Serial No. PCT/EP2020/069465, Written Opinion dated Aug. 28, 2020", (Aug. 28, 2020), 6 pgs.

"United Kingdom Application Serial No. 1909848.2, Search Report dated Nov. 29, 2019", (Nov. 29, 2019), 6 pgs.

* cited by examiner

METHODS FOR USE WITH A COMPONENT OF A BEAM LIMITING DEVICE

PRIORITY APPLICATIONS

This application is a U.S. National Stage Filing under 35 U.S.C. § 371 from International Application No. PCT/EP2020/069465, filed on Jul. 9, 2020, and published as WO2021/005188 on Jan. 14, 2021, which claims the benefit of priority to United Kingdom Application No. 1909848.2, filed on Jul. 9, 2019; the benefit of priority of each of which is hereby claimed herein, and which applications and publication are hereby incorporated herein by reference in their entireties.

This disclosure relates to the field of predictive maintenance, and in particular to a method of determining whether to schedule repair or replacement of a component of a beam limiting device such as a multileaf collimator.

BACKGROUND

Radiotherapy is an important tool in modern cancer treatment. Radiotherapy devices are large, complex machines, with many moving parts and inter-operating mechanisms. Despite precision engineering and rigorous testing, some component parts of a radiotherapy device may start to degrade over their lifetime. This can sometimes lead to sub-optimal operation and even the occasional safety override.

If at any point during treatment a radiotherapy device starts to function outside of its normal operating parameters, a safety override or "interrupt" occurs, whereby the machine stops delivering radiation to ensure patient safety. Such an event is inconvenient, as it adds time to the treatment, and in some cases means the treatment session must finish prematurely. Unplanned equipment downtime can disrupt planned treatment schedules, and may be expensive for the machine owner, be it due to loss of revenue, servicing and repair costs, or both.

It has been surmised that predictive maintenance and/or remote diagnostic techniques could be applied to radiotherapy machines. However, given the complexity of the machines and the sheer volume of data which may be gathered during operation, it is difficult to know how to analyse any available data to inform the predictive maintenance techniques. For example, while particular data patterns may be indicative of a particular fault or indicative that a particular component has degraded to a degree that it will shortly begin operation outside of its optimal operating parameters, identifying the link between particular data patterns and the particular fault or degrading component is often non-intuitive even for experienced service engineers. Even when a problematic machine is identified, trying to ascertain the nature of the fault is very difficult given the abundance of data and the complex interrelationships between the various components of the machine. In other words, even if a wealth of data from a radiotherapy device is available, remotely determining the nature of a fault or assessing the condition of a particular component is not a trivial matter.

The present disclosure relates generally to identifying that a component of a beam limiting device in a radiotherapy device is either operating in a non-optimal manner, is showing signs that it will soon be operating in a non-optimal manner, or else is nearing the time at which it should be replaced or repaired. To date, no such predictive approach has been possible, and existing methods of servicing and repair involve noting that a particular device has undergone multiple safety overrides, and sending a field service engineer to inspect the machine and diagnose and fix the problem. Often, the type of problem or the component which is at fault is not known in advance, and hence time consuming diagnostic testing must be performed on-site. Existing methods therefore result in a significant amount of machine down time. Also, in existing methods, a field service engineer is not made aware of a potential issue until the component has degraded to a point where the radiotherapy machine is undergoing safety interrupts, or even until the point where the radiotherapy machine can no longer operate within its safety parameters at all. This means that the servicing of the radiotherapy machine is often scheduled at a time which is inconvenient, or inefficient in terms of both field service engineer resources and the resources of the hospital or other machine owner.

The present invention seeks to address these and other disadvantages encountered in the prior art by providing a method of determining, preferably remotely, whether repair or replacement of a component of a beam limiting device such as a multileaf collimator (MLC) in a radiotherapy device should be scheduled.

SUMMARY

An invention is set out in the independent claims Optional features are set out in the dependent claims

FIGURES

Specific embodiments are now described, by way of example only, with reference to the drawings, in which.

Figure 4A:
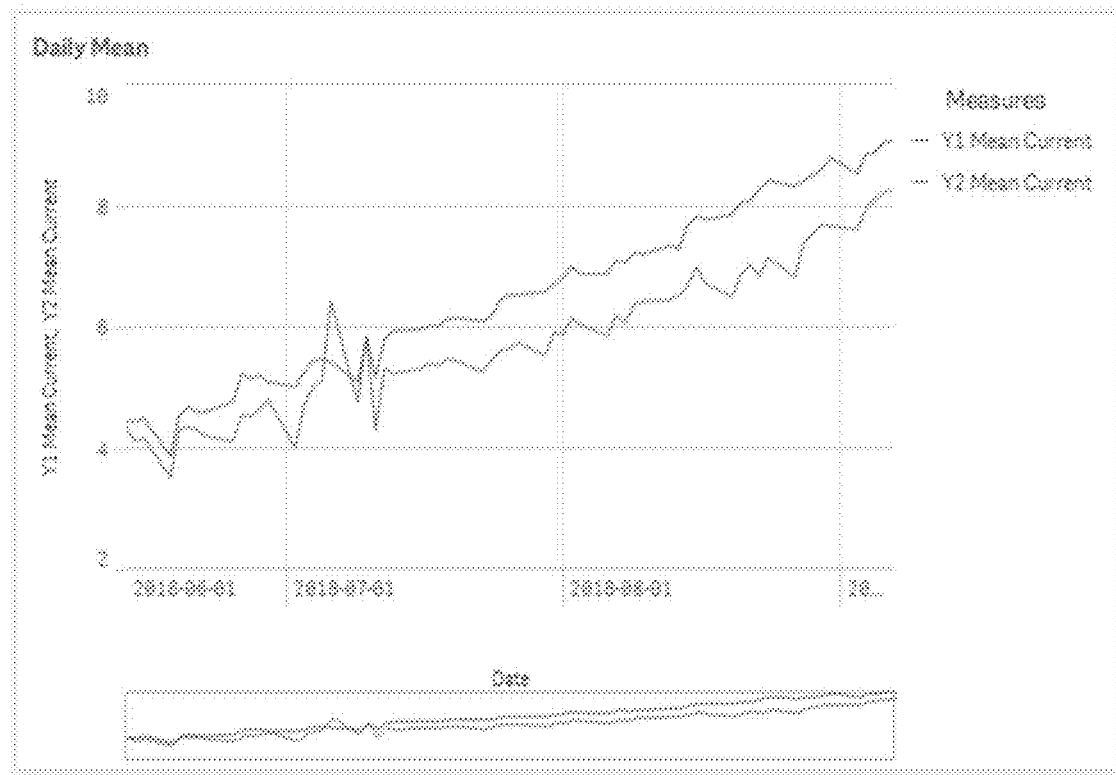
Figure 4B:
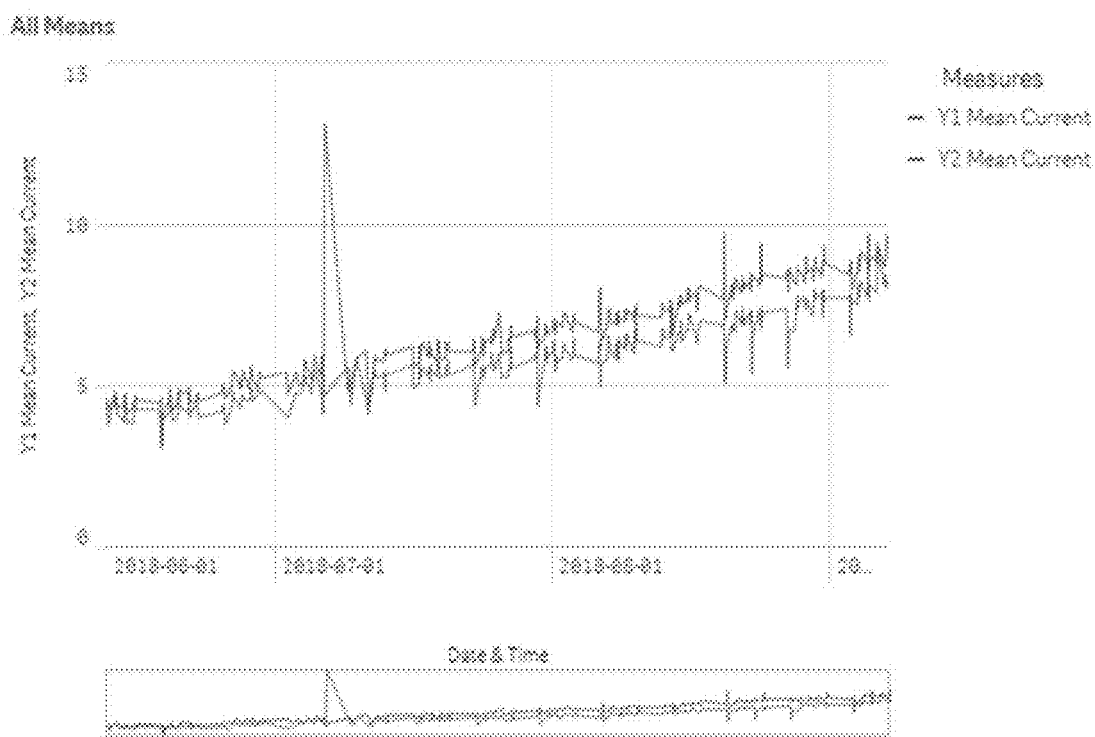
Figure 4C:
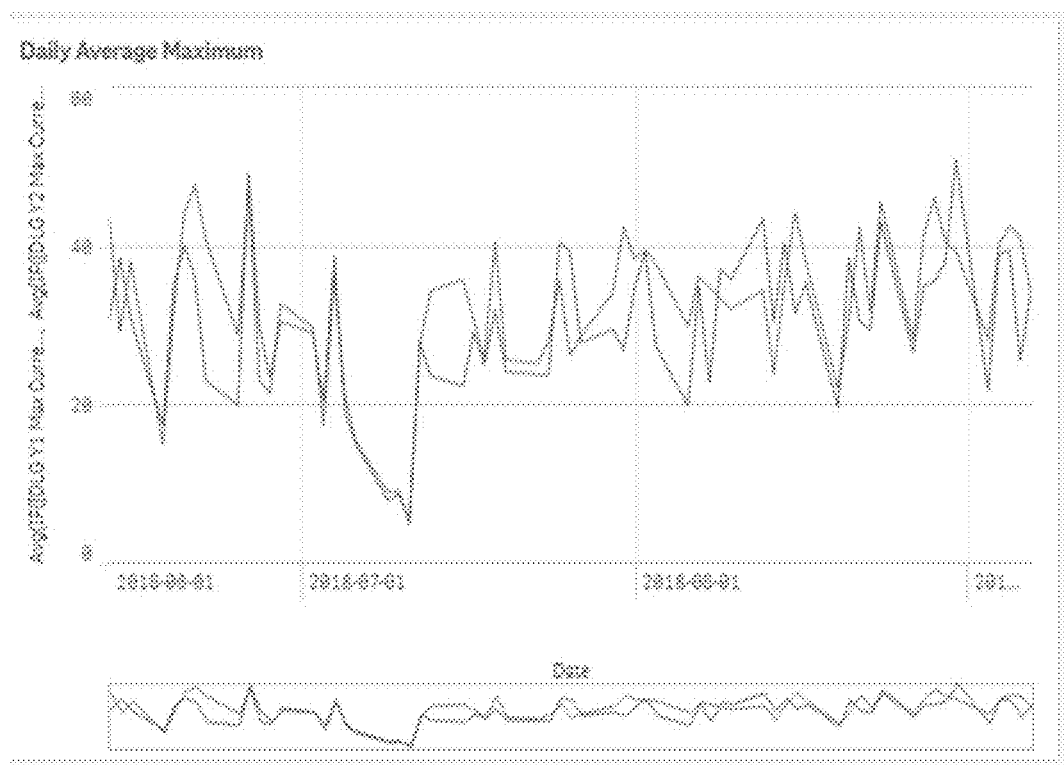
Figure 5:
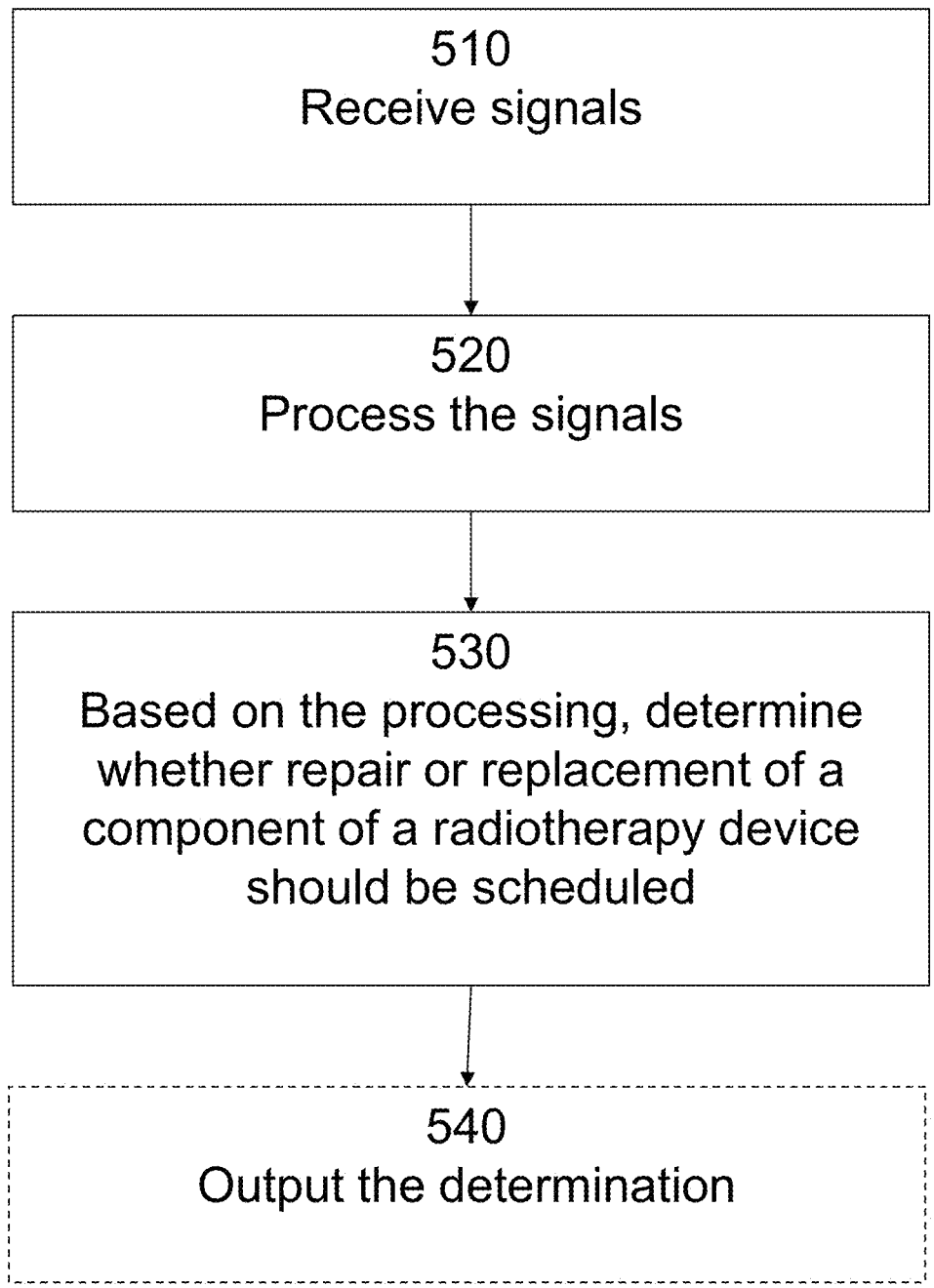
Figure 6:
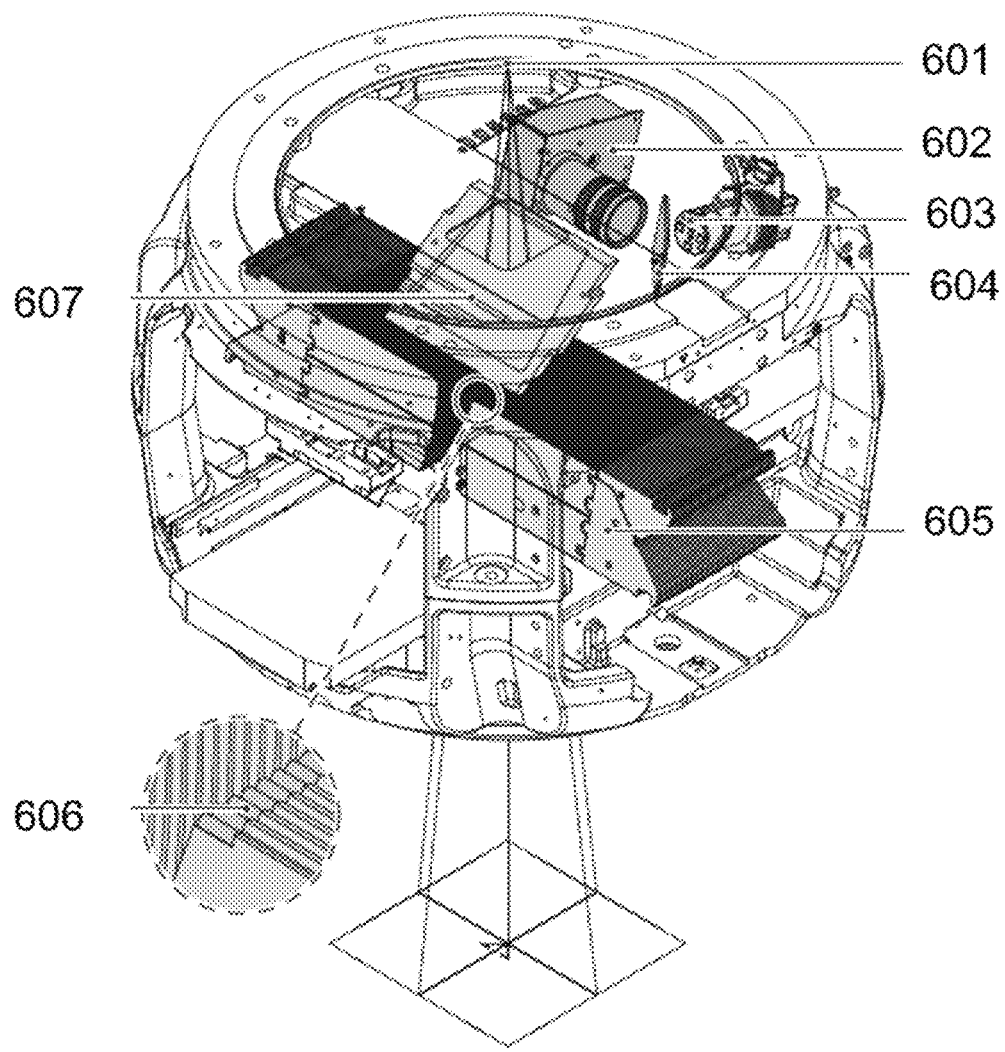
Figure 7A:
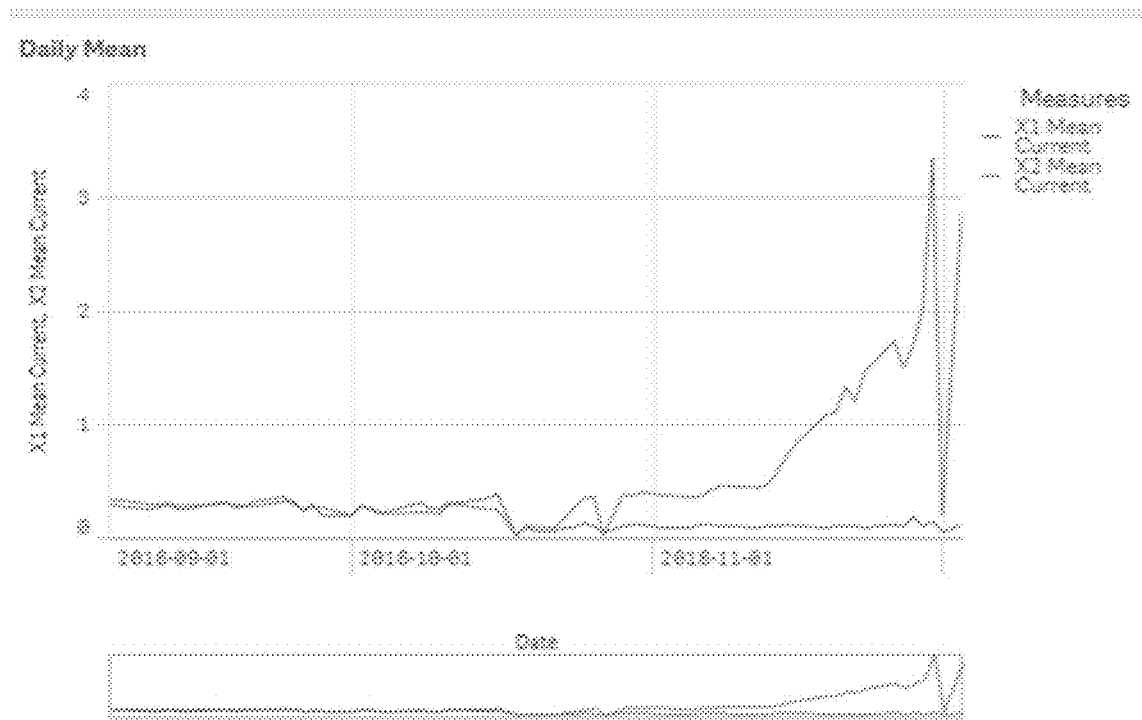
Figure 7B:
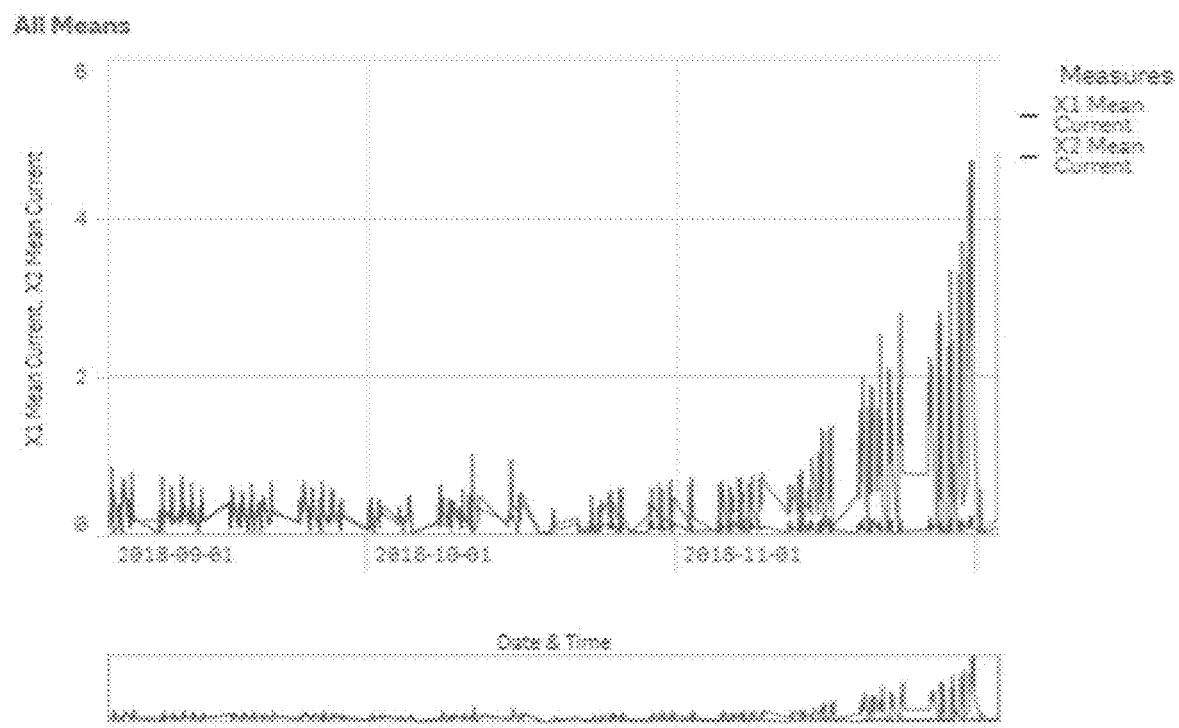
Figure 7C:
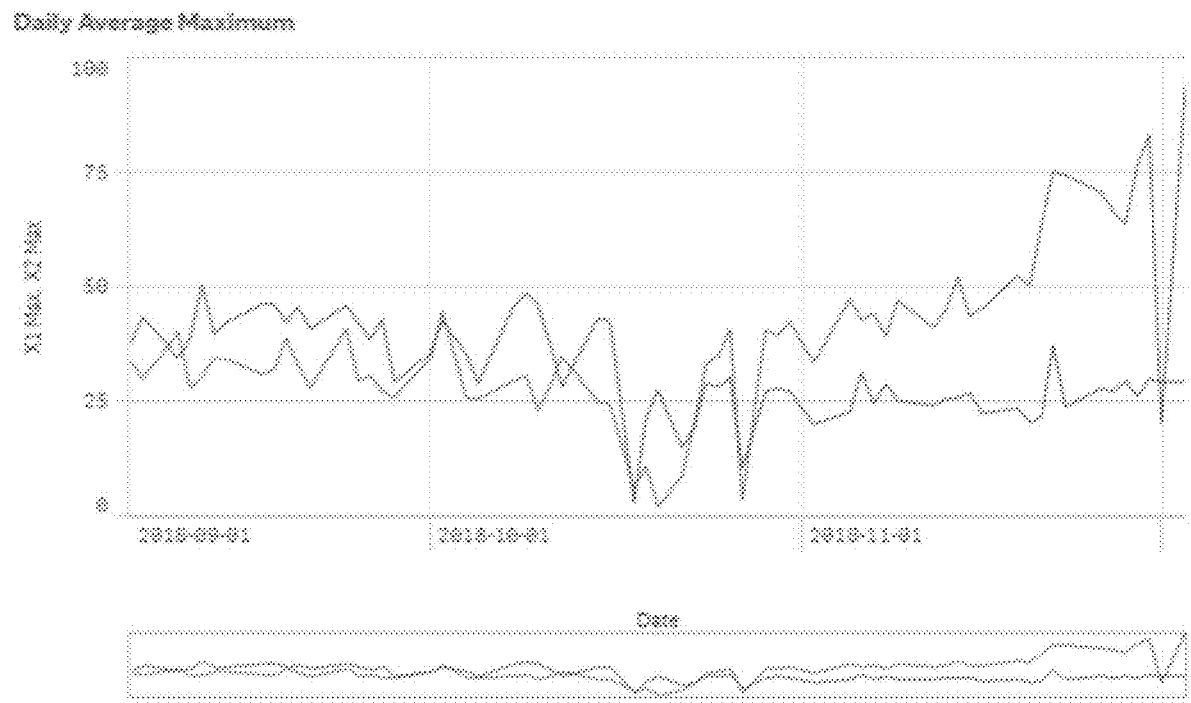

FIGS. 4a-c are graphs displayed data produced by methods according to the present disclosure;

FIG. 5 is a flowchart which depicts a method according to the present disclosure;

FIG. 6 depicts a beam limiting device comprising a position determining apparatus;

FIGS. 7a-c are graphs displayed data produced by methods according to the present disclosure.

DETAILED DESCRIPTION

The present disclosure relates to determining whether a component of a radiotherapy machine or device should be replaced, and/or to determining to what degree such a component is operating within safety limits and operational parameters. The radiotherapy device may be suitable for delivering a beam of radiation to a patient in order to treat a tumour. An example of a radiation source for producing a therapeutic beam of radiation is a linear accelerator (linac). Clinical linac devices are configured to deliver high energy radiation to a patient.

Radiotherapy machines are beginning to be configured to produce and record a large amount of data as they operate. For example, radiotherapy machines are configured to provide sensor readings from a variety of different sensors.

These sensors produce data which can be stored in a database. Radiotherapy devices may also be configured to allow remote connection, enabling service engineers to access a wealth of information about any connected machine without having to travel to the site where the machine is located. It is expected that, in many cases, machines may be returned to optimal performance without an engineer ever having to physically interact with the machine. However, there will still be occasions where the fault cannot be fixed remotely, and an engineer must be sent to: inspect the machine; determine the nature of the fault; and perform any maintenance required. If the repair involves replacing a part, further machine downtime is required before the machine can be brought back online.

The present methods involve evaluating the condition and/or performance of a component of radiotherapy equipment during its operation in order to identify and determine, preferably remotely, whether the component is nearing the end of its operational life and thus whether the component should be replaced or repaired. In particular, the present application relates to determining whether a component of a beam limiting device (BLD) such as a multileaf collimator (MLC) or a part thereof is approaching the end of its operational life. These components include drive PCBs and drive electronics, leaf guides, position sensing systems, and motors/actuators which are configured to actuate the leaves into and out from the radiation field in a manner which will be described below. Such techniques are advantageous as they allow a manufacturer or maintenance service provider to attend the machine knowing what will be required to fix the machine prior to arrival. The disclosed techniques allow the operation of components to be monitored, and hence components which are approaching the end of their operational life but which are still operating within required safety parameters can be identified. This in turn allows, for example, repair and/or replacement of the identified component to be scheduled for the next convenient service point. The disclosed methods help to reduce machine downtime and thereby minimise disruption to the machine's normal operation. The disclosed techniques can also be used to more effectively plan machine downtime for times which are more convenient or cost-effective for the owner of the equipment and/or the patients.

Figure 1:
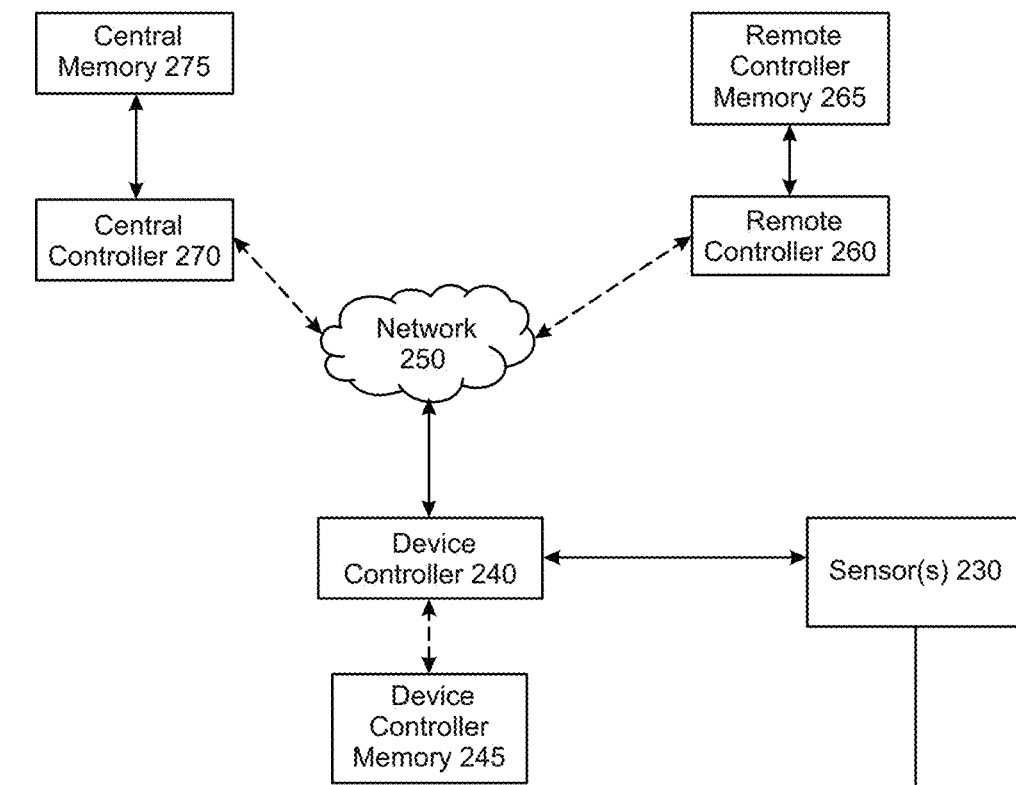
FIG. 1 depicts a system comprising a remote controller communicatively coupled to a central controller via a network, and also comprising a radiotherapy apparatus comprising a linac.
Figure 1:
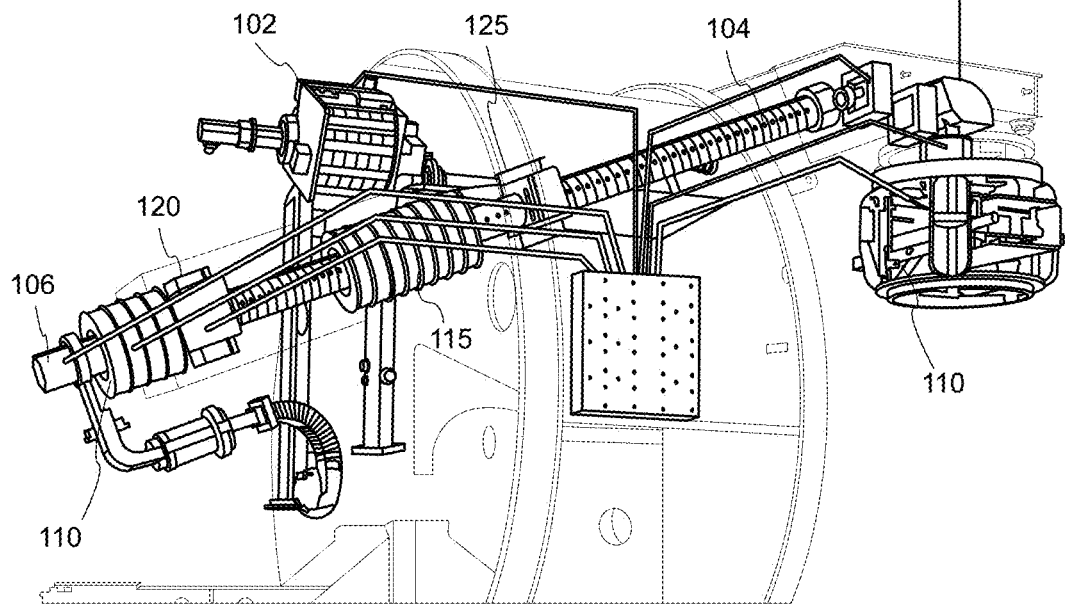

FIG. 1 depicts a cross-section of a radiotherapy device comprising a linac. The device is suitable for delivering, and configured to deliver, a beam of radiation to a patient during radiotherapy treatment. In operation, the linac device produces and shapes a beam of radiation and directs it toward a target region within the patient's body in accordance with a radiotherapy treatment plan.

A medical linac machine is by necessity complex, with many inter-operating component parts. A brief summary of the operation of a typical linac will be given with respect to the linac device depicted in FIG. 1. This summary is to provide useful context to the presently disclosed techniques and should not be considered as limiting on the scope of the present application as the presently disclosed techniques may be used in conjunction with any radiotherapy device.

The radiotherapy device/apparatus depicted in FIG. 1 comprises a source of radiofrequency waves, a waveguide, a source of electrons, a system capable of creating a strong vacuum comprising one or more vacuum pumps, a heavy metal target which produces X-rays when hit by an electron beam, and a complex arrangement of magnets capable of re-directing and focusing the electron beam onto the target. The device depicted in FIG. 1 also comprises a treatment head which houses various apparatus configured to, for example, collimate and shape the resultant X-ray beam. For example, the treatment head may contain a primary beam limiting device (BLD) and a secondary BLD. The primary BLD may be a primary collimator, which acts to form the radiation emitted from the target into a beam by blocking radiation emitted at wide angles. The secondary BLD may be a secondary collimator such as an MLC, which will be described in greater detail elsewhere herein. The BLD may also comprise one or more diaphragms configured to be extended into and withdrawn from the radiation field in order to limit and shape the beam. The diaphragm and MLC leaves are configured to move in directions which are substantially perpendicular to one another. The treatment head may also comprise an ion chamber or other dosimeter configured to provide information about the radiation as it passes through the dosimeter.

The source 102 of radiofrequency waves, such as a magnetron, produces radiofrequency waves. The source 102 of radiofrequency waves is coupled to the waveguide 104, and is configured to pulse radiofrequency waves into the waveguide 104. Radiofrequency waves pass from the source 102 of radiofrequency waves through an RF input window and into an RF input connecting pipe or tube. A source 106 of electrons, such as an electron gun, is coupled to the waveguide 104 and is configured to inject electrons into the waveguide 104. In the source 106 of electrons, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the radiofrequency wave source 102, electron source 106 and the waveguide 104 is such that the radiofrequency waves accelerate the electrons to very high energies as they propagate through the waveguide 104.

The design of the waveguide 104 depends on whether the linac accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104. As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets. The electron beam may be focused by a first arrangement of focusing magnets 110 and a second arrangement of focusing magnets 115. The beam is 'steered', i.e. directed, by a first arrangement of steering magnets 120 and a second arrangement of steering magnets 125. The electron gun 106, waveguide, and flight tube are kept under high vacuum conditions by a vacuum system or suitable vacuum apparatus.

Once the electrons have been accelerated, they pass into a flight tube. The flight tube may be connected to the waveguide by a connecting tube. This connecting tube or connecting structure may be called a drift tube. The flight tube is kept under vacuum conditions by the pump system. The electrons travel along a slalom path toward the heavy metal target. The target may comprise, for example, tungsten. Whilst the electrons travel through the flight tube, an arrangement of focusing magnets act to direct and focus the beam on the target. The slalom path allows the overall length of the linac to be reduced while ensuring that the beam of accelerated electrons, which is comprised of electrons with a small spread of energies, is focused on the target.

To ensure that propagation of the electrons is not impeded as the electron beam travels toward the target, the waveguide 104 is evacuated using a vacuum system comprising a vacuum pump or an arrangement of vacuum pumps. The pump system is capable of producing ultra-high vacuum (UHV) conditions in the waveguide 104 and in the flight tube. The vacuum system also ensures UHV conditions in the electron gun. Electrons can be accelerated to speeds approaching the speed of light in the evacuated waveguide 104. Together, the electron gun 106, waveguide 104 and the flight tube form a vacuum tube in which electrons can be accelerated and directed toward a target in vacuum conditions.

When the high energy electrons hit the target, X-rays are produced in a variety of directions. The target is located inside the flight tube, and is located at the end of the flight tube to seal the vacuum system. The flight tube also comprises a target window, which is transparent to X-rays, which his positioned to allow the X-rays which are produced when the linac is in operation to pass from the evacuated flight tube through the target window and into the treatment head 110. At this point, a primary collimator blocks X-rays travelling in certain directions and passes only forward travelling X-rays to produce a cone shaped beam. The X-rays are filtered, and then pass through one or more ion chambers for dose measuring. The beam can be shaped in various ways by beam-shaping apparatus, for example by using a multi-leaf collimator, before it passes into the patient as part of radiotherapy treatment.

In some implementations, the linac is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The linac device also comprises several other components and systems. The whole system is cooled by a water cooling system (not shown in the figures). The water cooling system may be used, in particular, to cool the waveguide 104, target, and radiofrequency source 102. In order to ensure the linac does not leak radiation, appropriate shielding is also provided. As will be understood by the person skilled in the art, a linac device used for radiotherapy treatment will have additional apparatus such as a gantry to support and rotate the linac, a patient support surface, and a controller or processor configured to control the linac apparatus.

The linac also comprises one or more sensors 230. Each sensor 230 is configured to measure, record or otherwise determine a value related to the performance of a particular component of the radiotherapy device, and communicate a signal to the device controller 240 indicative of the value. For example, the one or more sensors 230 may comprise a current sensor, e.g. an ammeter, configured to provide a measurement indicative of the current supplied to an MLC guide motor. For example, the current sensor 230 may be suitable for detecting, and be configured to detect, currents supplied to the MLC, and in particular to the DLG of the MLC. The one or more sensors 230 may comprise a current sensor configured to provide a signal indicative of current supplied to a source of illumination in an MLC leaf position determining system. The one or more sensors 230 may comprise a temperature sensor configured to provide a signal indicative of temperature at the source of illumination. The one or more sensors may comprise a current sensor configured to produce a signal indicative of the current supplied to a diaphragm actuation means of a diaphragm apparatus.

The one or more sensors 230 may be comprised within the treatment head 110. The one or more sensors 230 are communicatively coupled with a device controller 240, for example via a dedicated PCB, and data relating to components of the radiotherapy device is communicated to the device controller 240. For example, the current supplied to the DLG is measured by a current sensor 230 and communicated to the device controller 240 with a particular frequency or regularity, for example the current sensor 230 may provide a current measurement to the device controller 240 every second. The data supplied may be indicative of the current supplied, and the device controller 240 or other controller or processor may be configured to determine or derive the current supplied from the indicative value.

With reference to FIG. 1, the sensors described herein comprise means with which to communicate with the device controller 240. For example, the one or more sensor 230 may comprise suitable processing circuitry and transmitting antennas. The one or more sensor is electronically and/or communicatively coupled to the device controller 240. The device controller 240 receives signals from the one or more sensor 230 as they are generated, or produced, by the one or more sensor 230. The device controller 240 is electronically and/or communicatively coupled to a device controller memory 245. The device controller 240 and device controller memory 245 may be configured to store signals generated by the current sensor. The generated signals from the current sensor comprise sensor data. The one or more sensor 230 may be described as sensing means.

By way of an example, both the current sensor and the temperature sensor coupled with the source of illumination in the MLC leaf position determining apparatus (not shown in FIG. 2) comprise means with which to communicate with the device controller 240.

The device controller 240 is communicatively coupled to a central controller 270, for example via a network 250. The device controller 240 is configured to transmit, i.e. send, the sensor data to the central controller 270 to be stored on the central controller memory 275. The central memory 275 may comprise a number of different servers as part of a cloud storage solution. The central controller may be communicatively coupled to a plurality of radiotherapy devices via network 250, each of which are configured to transmit signals to the central controller 270 to be stored on central memory 275. Central controller 270 is adapted and configured to process received signals and store them in a database. Processing the signals may comprise, for example, calculating and storing daily averages of particular sensor data.

The radiotherapy device has a variety of sensors, the signals/readings from which are communicated to the device controller 240. The signals may be stored in the device controller memory 245 and/or may be communicated via the network to the central controller 270. The data may be uploaded to the central controller 270 as it is generated, or may be stored on the device controller memory 245 in order to be uploaded as a batch upload, for example at regular time intervals. Alternatively, the data may be continuously gathered by the device controller 240, for example the sensor signals may be sampled every 4 seconds while the device is not delivering radiation, and data is uploaded if the data shows a particular variance from the previously uploaded data point. In a specific implementation, the data points are uploaded when there is a change of +/−0.04 A, and the device controller looks for a new data item once every 4 seconds while the device is not delivering radiation, and once every second while the linac is delivering radiation.

The data is stored in a database on central memory 275, which may comprise data from sensors, for example the data includes the current values as denoted by signals from the current sensor, the degree of rotation of the gantry, whether or not radiation is being delivered at a particular time and the dose rate and machine output as indicated by a dosimeter or monitor chamber, as well as the water temperature at various points around the water cooling system. These types of data are given to provide examples, and the skilled person will appreciate that a modern linac device may be configured to generate a wealth of data from a large variety of sensors.

The device controller 240 and central controller 270 are both also communicatively coupled to a remote controller 240. The remote controller 260 may access the central database, which stores information and data regarding a plurality of radiotherapy devices, through the database 250 and by using a suitable software platform. The remote controller 260 may also access the device controller 240 to obtain real-time information regarding a particular radiotherapy machine.

In an implementation, the device controller 240 receives signals from the one or more sensors 230 and transmits them to the remote controller 260. The central controller 270 receives the signals and then derives a value from the signals, for example by calculating the average current value from the current signals over a time period. The average current values may be stored on the central controller memory 270. Processing of the values then takes place when the remote controller 260 accesses the central memory 275 via the network 250. However, at least some of the steps, and in some examples all of the steps, displayed in FIG. 4 may be performed on the device controller 240. It will be appreciated that any combination of the device controller 260, central controller 270 and remote controller 260 may be used to perform the disclosed methods.

The methods of the present disclosure may be performed on a regular basis, for example daily, in order to continuously monitor whether a component of a radiotherapy device should be repaired or replacement, or at least scheduled for repair or replacement.

The device, central and remote controllers may each be described as a processor, computer, or computing device. The controllers may be connected (e.g., networked) to each other and/or to other machines in a Local Area Network (LAN), an intranet, an extranet, or the Internet. The controllers may each operate in the capacity of a server or a client machine in a client-server network environment, or as a peer machine in a peer-to-peer (or distributed) network environment. The controllers may each be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, respective controllers are illustrated, the term "controller" shall also be taken to include any collection of machines (e.g., computers) that individually or jointly execute a set (or multiple sets) of instructions to perform any one or more of the methodologies discussed herein.

The approaches of the present disclosure may be embodied on one or more of the device controller memory and the remote controller memory, or any other computer-readable medium. The medium may be a non-transitory computer-readable medium. The computer-readable medium carries computer-readable instructions arranged for execution upon a processor so as to make the controller/processor carry out any or all of the methods described herein. The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

The approaches of the present disclosure may be performed by a processor of a device, hereby the processor is coupled with a computer-readable memory, the memory comprising computer-executable instructions which, when executed by the processor, cause the processor to perform any of the approaches and methods of the present disclosure.

Figure 2:
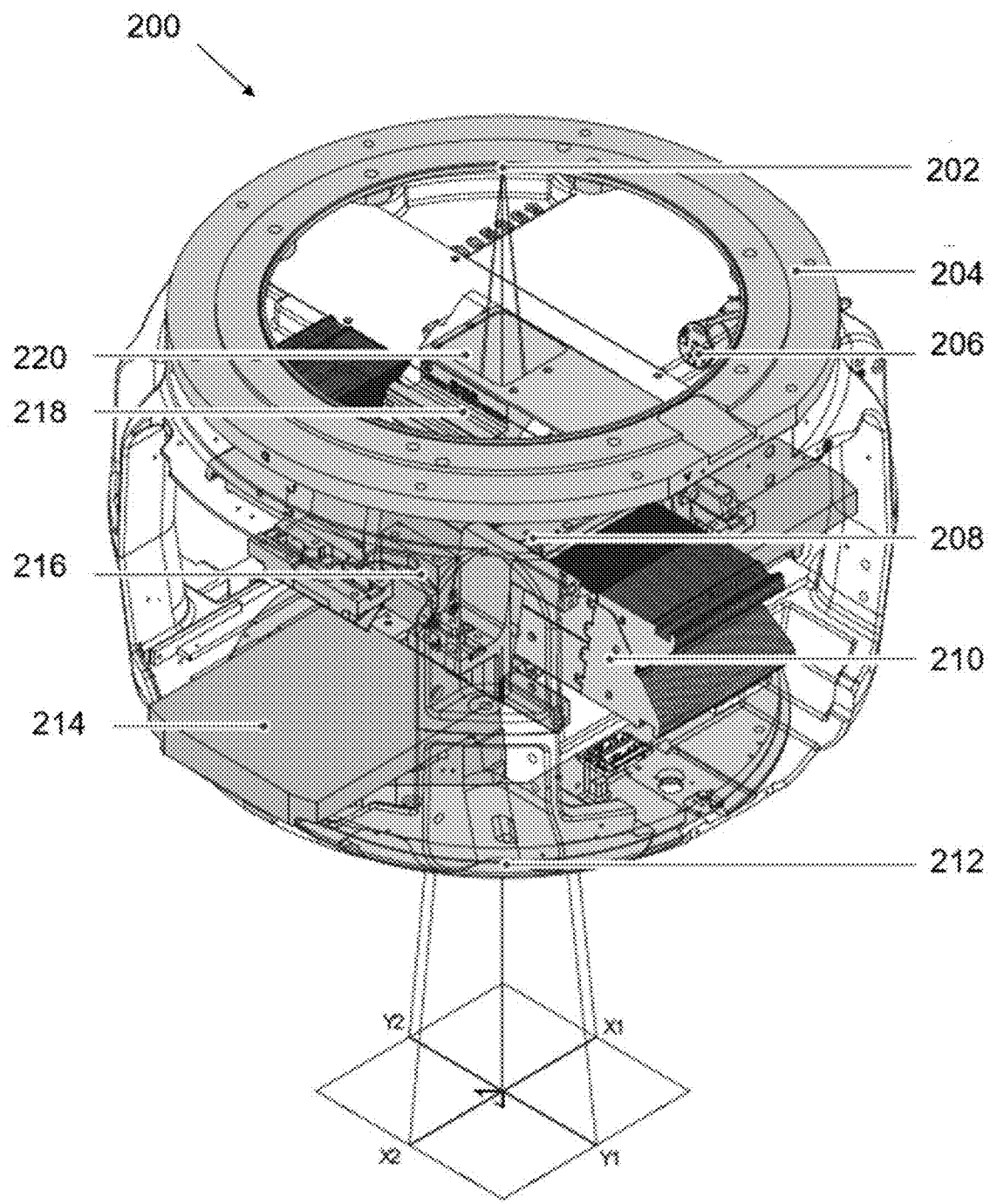
FIG. 2 depicts a beam limiting device comprising a multi-leaf collimator and diaphragm apparatus.

Description of specific apparatus relevant to the predictive MLC/DLG method FIG. 2 depicts an example of a beam limiting device (BLD) 200. FIG. 2 schematically depicts the position of the target 202, from which X-rays are produced, and schematically shows the beam passing through the BLD 200. The BLD 200 comprises an interface ring 204 configured to allow the BLD to be attached to other components of the treatment head, for example an ion chamber and/or dosimeter. The BLD 200 also comprises a source of illumination such as a projector which forms part of an optical detection system which has the purpose of detecting the location of each of the leaves of the MLC, including those forming part of the leaf bank 210 shown in FIG. 2. As will be better appreciated upon inspection of FIGS. 3a and 3b, the BLD 200 comprises two banks of leaves which face each other across the radiation field. Each bank comprises a plurality of leaves. For example, in a particular implementation each bank comprises 80 leaves.

The MLC comprises a dynamic leaf guide (DLG). The dynamic leaf guide comprises a leaf bank support, leaf bank actuation means, and guide means. The leaf banks are each supported on a respective leaf bank support. Each leaf bank support is configured and structured so as to provide support for the entire bank of leaves. The leaf bank actuation means is configured to move the entire bank of leaves such that the bank of leaves may be extended into, and withdrawn from, the radiation field. The leaf bank actuation means is configured to move the leaf bank support along guide means. The guide means may be referred to as a leaf bank guide, and may comprise a guide rail or ridge. The leaf bank actuation means, which may be described as a leaf bank guide motor or DLG motor, is configured to extend the leaf bank along the leaf bank guide into the path of a radiation beam. In other words, each DLG is configured such that, upon actuation of the DLG motor, each leaf in the leaf bank is moved by an equal amount into, or out from, the path of the beam in a direction defined by the guide. Additionally, the MLC may comprise a guide brake configured to halt the movement of the leaf bank along the guide when the bank has reached the required position.

In addition to movement of the leaf bank via the DLG, each leaf is individually actuatable, for example by a suitable arrangement of lead screws and leaf actuators/leaf motors. The MLC comprises leaf actuation means by which each individual leaf can be independently extended into, and withdrawn from, the radiation field. The leaf actuation means may comprise leaf motors and an arrangement of lead screws. Various arrangements for providing actuation of the leaves of MLCs are known to the skilled person and will not be discussed in detail herein. During treatment, when the MLC collimates the beam to form a particular beam shape, for example in accordance with a treatment plan, the DLGs move the leaf banks forward into the radiation field. Once the banks are in the correct position, each leaf is individually actuated so as to form the desired shape. In other words, the MLC presents an edge to the radiation beam which can be varied so as to provide a particular beam shape.

The BLD 200 further comprises: an accessory ring 212 for attachment of accessories to the BLD 200; side shielding 216 to prevent radiation from leaking from the BLD 200; a wedge filter 218; and a shutter 220. The wedge assembly 314 can be seen in FIG. 3b.

The radiotherapy device also comprises current sensing means configured to provide signals indicative of the current supplied to the leaf bank actuation means/guide motor, and to communicate those signals to the device controller as explained elsewhere herein with respect to FIG. 2.

Figure 3A:
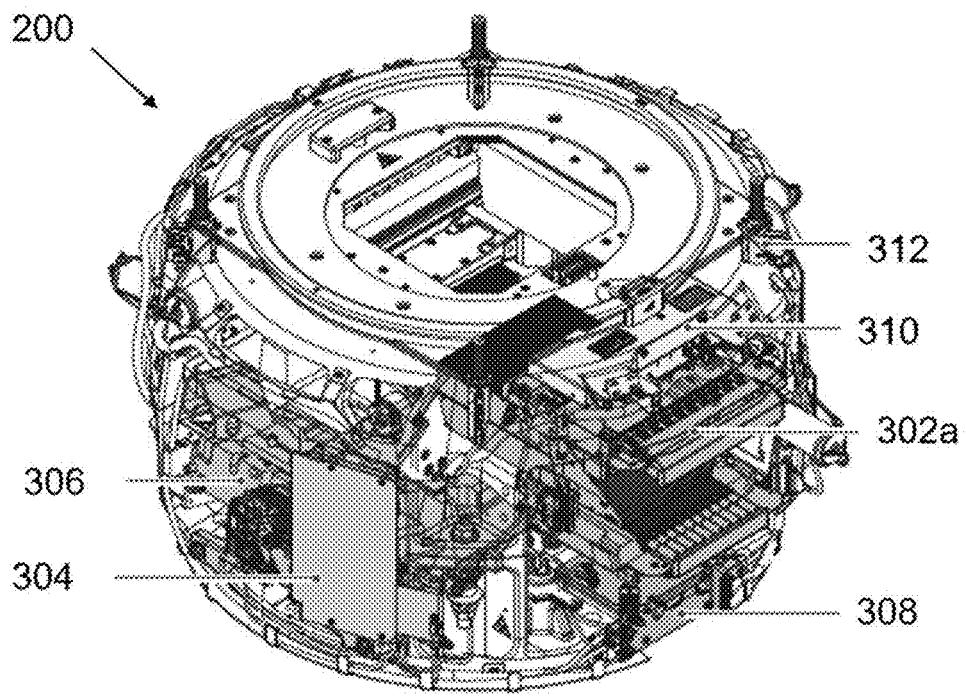
FIGS. 3a and 3b depict the beam limiting device of FIG. 2 but at different angles and with different components highlighted.
Figure 3B:
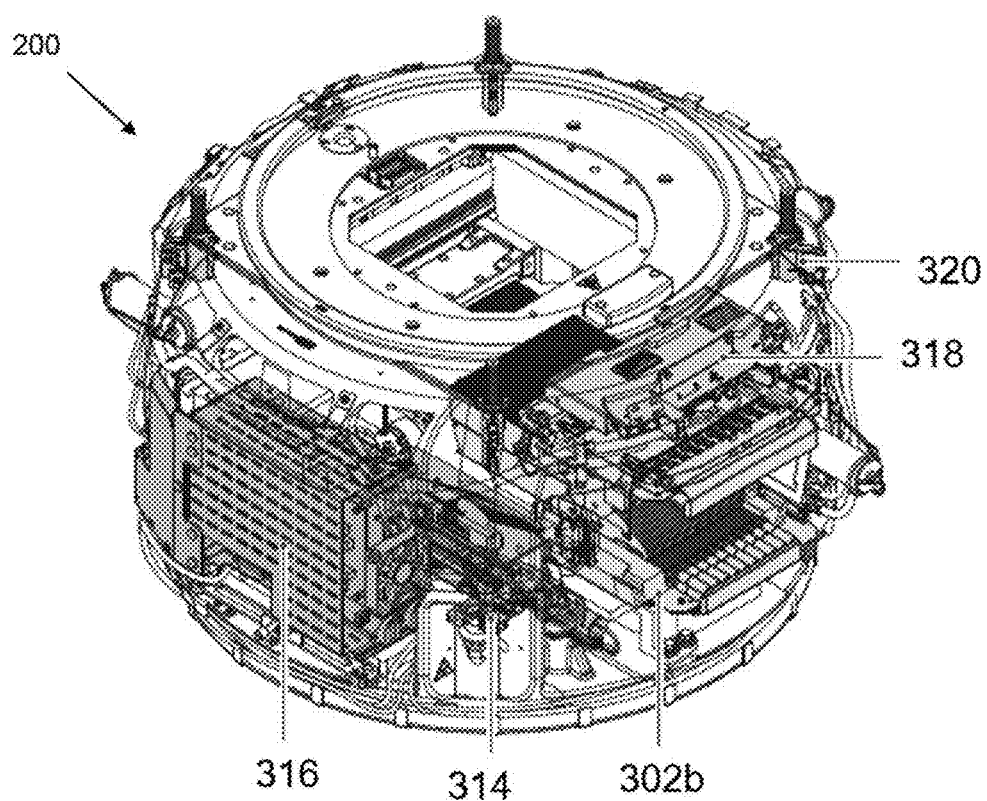

FIGS. 3a and 3b depict the beam limiting device 200 of FIG. 2, with different internal components highlighted. FIG. 3b shows the BLD rotated through an angle of roughly 180 degrees from the view depicted in FIG. 3a so that both sides of the BLD can be seen. Beam limiting device 200 comprises a first leaf bank 302a, which can be better seen in FIG. 3a, and a second leaf bank 302b, which can be better seen in FIG. 3b. In terminology used by the applicant, the first leaf bank 302a may be described as a Y1 leaf bank 302a and the second leaf bank 302b may be described as a Y2 leaf bank.

The BLD 200 comprises a DLG PCB cage 304 configured to hold a DLG PCB in place. The DLG PCB may be described as a drive PCB. The drive PCB is configured to control movement of the leaf guide e.g. via the guide motor. The drive PCB may therefore hold a microprocessor and circuitry configured to receive and action control signals received from a separate control means. An optics assembly 306 forms part of the optical detection system which allows the movement of each of the leaves to be tracked. The BLD 200 comprises a plurality of PCBs, including a signal and power PCB 308 which controls signals received by and sent to the BLD and also the power provided to each component, an accessory PCB 310, a diaphragm PCB 318, and a router, CCU, wedge and LED PCB which is held by cage 316. The PCBs are each configured to control operation of the components to which they are connected in a known manner. The BLD 200 also comprises: a touchguard actuator 320, which forms part of a touchguard system which is configured to detect if the treatment head is in close proximity to the patient or another object so as to avoid collision, and a touchguard actuator 312.

The current supplied to each DLG 208 is monitored by a suitable current sensor 230, current sensors, or current sensing means. The current sensor may form part of, or may be comprised within, the DLG PCB. In terminology used by the applicant, the current supplied to the first DLG 302a may be called the Y1 current, and the current supplied to the second DLG 302b may be called the Y2 current. In more detail, the current supplied to the first DLG 302a is the current supplied to a first DLG motor within the first DLG 302a, and so the Y1 current is a measure of the current required in order to actuate the first leaf bank 32a into position.

While reference is primarily made to the Y1 current herein, it will be appreciated that the Y2 current, and values derived therefrom, is equivalent to the Y1 current except that the Y2 current is associated with the second DLG 302b, which actuates the second leaf bank (the Y2 leaf bank), whereas the Y1 current is associated with the first DLG 302a.

The current sensor, which may be described as a current sensing means, may comprise any number of possible sensors which are suitable to measure the current supplied to the MLC of the BLD, and in particular to the DLG of the MLC. It will be understood that the current sensor is a sensor configured to provide a signal, or value, which is indicative of the current supplied to the DLG.

Description of Apparatus Relevant to the Predictive Position Determining Apparatus/UV LED Method A further component of the BLD 200 and/or the MLC is a leaf position monitoring and/or detection system.

Such a system is depicted in FIG. 6 within the BLD. It is desirable to monitor the actual position of the leaves of the MLC in order to provide feedback and allow their position to be adjusted accurately. Such systems may be based on optical vision technology and/or the use of fluorescent markers. The skilled person will be aware of such systems, however for completeness a short description is provided below.

The leaf position monitoring system may comprise a source of light 603 such as an LED projector, a light detector 602 such as a camera, and one or more reflective markers 606 positioned on each leaf of the MLC. The source of UV light is also shown in FIG. 2 using reference numeral 206. FIG. 6 shows two banks of leaves, with one being labelled 605. The light detector 602 is configured and positioned to 'view' the reflective leaf markers 606. The system may also comprise reference markers which are not placed on an MLC leaf but which may be placed, for example, at particular positions within the field of view such as at the corners of the field of view. By shining light on the MLC leaves using the source of light 602, light is reflected from optical markers 606 on the MLC leaves and detected at the detector 602. Light is also reflected form the reference markers, which is also detected at the detector. Signals received at the detector may be processed in a known way to determine the position of each of the MLC leaves. The optical detection system may comprise a number of mirrors 607 in order to allow illumination of the MLC leaves and to direct reflected light to the detector.

The MLC leaf position monitoring system may alternatively, or additionally, make use of fluorescent markers placed on each MLC leaf. These markers may also be described as optical markers 606. Again with reference to FIG. 6, a suitable fluorescent marker may be comprised of ruby. In an example implementation, ruby markers 606 may be illuminated by a source of light 602 (e.g. a 410 nm monochromatic source). This source of light 602 may be, for example, an LED. The LED may be configured to emit light in the UV range, in particular if the fluorescent markers 606 on the leaves are rubies. This will cause the ruby marker to fluoresce, emitting light in a variety of directions and onto a dichroic beamsplitter 604 which diverts a proportion of the light to a camera 602 protected by an infra-red pass filter. This IR pass filter will limit the light incident on the camera to that emitted by the fluorescent ruby markers 606. By using reference markers in the same manner as described above it is possible to determine the position of each of the fluorescent markers and hence determine the position of each of the MLC leaves. In a particular implementation, ultraviolet light from an LED source produces infrared fluorescence when it falls on the ruby tips 606 of the multileaf collimator leaves. This infrared fluorescence, detected by an infrared camera 602, is used to reliably monitor and accurately position the leaves and can be viewed in realtime on the linear accelerator's display screen.

More generally, the radiotherapy device/apparatus may comprise a multi-leaf collimator, and a position determining apparatus which is configured to determine the position of one or more leaves of a multi-leaf collimator. Each of the one or more leaves comprises an optical marker. The position determining device comprises a source of illumination configured to illuminate the one or more leaves, and a light detection means, configured to detect light received from the optical markers. The source of illumination may be referred to as a light source. While reference is made to 'optical' and 'light', it will be understood that the system is not limited to use of illumination in the visible part of the spectrum. The optical marker is configured to reflect the illumination and/or fluoresce at the wavelength of illumination.

The position determining apparatus/device further comprises a control means, and current sensing means configured to provide a signal indicative of current supplied to the source of illumination. This may be a current sensor such as an ammeter. The position determining device further comprises temperature sensing means configured to provide a signal indicative of temperature at the source of illumination. The temperature sensing means may be a temperature sensor of a known type such as a thermocouple, semiconductor temperature sensor, or a resistance temperature detector.

The control means controls a feedback loop. The light detection means is configured to produce a signal indicative of the amount, or intensity, of light received by the light detection means. The control means receives this signal. Based on this signal, the control means determines whether the intensity of light produced, i.e. emitted, from the source of illumination should be increased. For example, the control means may subtract the value of the signal received from the light detection means from an expected or ideal signal to produce an error value. The greater the error value, the more current is supplied to the source of illumination so as to increase the intensity of light emitted by the source of illumination. It is important that the intensity and/or amount of light received from the optical markers on the leaves (whether it be via the process of fluorescence or reflection) is high enough such that the control means can determine the position of each leaf with sufficient accuracy. This feedback loop is useful in instances where, for example, the amount of light received at the light detection means is not high enough make this determination with sufficient accuracy. For example, the optical markers on the leaves and/or an optical component of the light detection means such as a lens may be dirty or dusty, leading the light received at, and the signal produced by, the light detection means to be reduced. Increasing the intensity of light emitted by the source of illumination can act to offset and mitigate this reduction in signal.

Alternatively, the source of illumination itself may not be working optimally, or the control means (such as a PCB) may not be implementing the feedback loop properly.

Hence, an increase in the current supplied to the source of illumination by a control means configured to implement such a feedback loop is indicative that one of the components of the position determining apparatus is not working optimally and hence needs to be repaired or replaced. It may be that the source of illumination needs to be repaired or replaced, the PCB/control means may need to be repaired or replaced, and/or the optical components such as the leaf optical markers and/or the camera lens may need to be cleaned.

In an example implementation of the feedback loop, the light detection means is configured to produce and provide a signal indicative of the light received by the light detection means to a control means. The control means is configured to monitor signals received from the light detection means and control the current supplied to the source of illumination accordingly. This might be via a simple servo arrangement. In an example, if the received signals from the light detection means fall below a threshold value, the current supplied to the source of illumination is increased. Conversely, the current may be reduced if the signals from the light detection means exceed a threshold.

Description of Specific Apparatus Relevant to the Predictive Diaphragm Method

The beam limiting apparatus of the device also comprises a diaphragm apparatus. The diaphragm apparatus is configured to shape the beam of radiation, in a manner similar to the MLC. The diaphragm apparatus comprises one or more diaphragms 214 configured to be extended into, and withdrawn from, the radiation field. In an example, the diaphragm apparatus comprises two diaphragms 214 which face each other across the radiation field. The diaphragm apparatus further comprises diaphragm actuation means, for example a diaphragm motor, which is configured to effect this movement. The diaphragms may be configured to move in a movement axis which is generally or substantially perpendicular to the beam axis, and also generally or substantially perpendicular to the movement axis of the MLC leaves.

With reference to FIG. 2, it will be appreciated that the actuation means of the MLC is configured to move the MLC leaves 210 in the directions indicated as Y1 and Y2, and along a movement axis depicted in the figure as the 'Y' direction. The diaphragm apparatus is configured to move the diaphragms in directions X1 and X2, and along a movement axis depicted in the figure as the 'X' direction. While the diaphragm 214 depicted in FIG. 2 are positioned 'underneath' the MLC (i.e. farther away from the beam source 202), in alternative implementations the diaphragm may be positioned 'above' the MLC (i.e. closer to the beam source 202 than the MLC).

The diaphragm apparatus further comprises a control means, such as a PCB. The apparatus further comprises a current sensing means configured to provide a signal indicative of current supplied to the diaphragm actuation means. This may be a current sensor such as an ammeter. The current sensing means may form part of the control means and may be for example positioned on the PCB. The control means and current sensor may be similar in type to the other control means and current sensors described herein. The current sensor is communicatively coupled with the device controller 240 in a manner described generally for all sensors elsewhere herein and depicted in FIG. 2.

Predictive MLC/DLG Data and Method

FIGS. 4a-c show graphs generated using data provided by the current sensor described above. The data shown in the graphs may be determined during the processing step 520 in the flowchart of FIG. 5. The data may be stored in a central database stored on the central memory 275, which is accessible by, for example, the remote controller 265. The graph shows time along the X axis and current along the lefty axis. The graph demonstrates the type of signals which may be received from the device controller and which may be accessible by a remote controller. The graphs show data from a particular radiotherapy machine which has a multi-leaf collimator comprising at least one dynamic leaf guide which is approaching the end of its operational lifetime. In other words, it would be beneficial if one or more of the DLGs of this machine were scheduled for repair or replacement, otherwise the performance and condition of the DLGs will continue to degrade until the point where the multileaf collimator will cause the radiotherapy device to operate outside of its safety parameters, causing interruption to treatment and scheduling delays.

FIG. 4b shows the 'all means' plot, or 'hourly average' plot. The all means plot shows current values averaged over successive hours the machine is in operation. In other words, signals received from the sensor are averaged over a first time period, or time interval, of an hour. Each plotted point on the 'all means' graph is an averaged current value formed by averaging the current values connected with a particular DLG received in a particular hour the machine is in operation. The Y1 hourly mean plot is denoted in blue and is generally above the Y2 hourly mean current, shown in red. From inspection of the graph it will be appreciated that both the Y1 hourly mean current and the Y2 hourly mean current are increasing with time. Data points for hours in which the radiotherapy device is not in use are not shown in the graph, thus the graph comprises several peaks and troughs of activity while the device is in operation joined with flat lines which represent periods in which the device is not in operation. By regularly determining an average of the received Y1 (or Y2) current signals within a first time interval, e.g. an hour, a first plurality of averaged values is produced. This first plurality of averaged values can be described as hourly averaged values.

FIG. 4a shows the 'daily mean' current plot. The daily mean for a particular day is the average of each hourly average value, as plotted in FIG. 4b, in the particular day. This daily averaged current value can be determined for both the dynamic leaf guide of the first leaf bank (Y1 mean current), and separately for the second leaf bank (Y2 mean current). The Y1 mean current is denoted in blue and it will be appreciated that the Y1 current line of the particular machine in question is generally above the Y2 current line. The daily mean plots are made up of data points from every day the radiotherapy device is in operation. The daily Y1 mean for a particular day can be thought of as the average current supplied to the first DLG during that day. Each current value supplied by the current sensor and recorded in memory during a particular day in relation to the Y1 current is first averaged by the hour to produce a plurality of hourly mean values (shown in FIG. 4b), and the hourly mean values within the particular day are averaged to produce a daily mean or daily average. The Y2 daily mean value can be calculated in a similar manner, i.e. by averaging Y2 current values provided during a particular day in the manner described. Upon inspection of FIG. 4a, it will be appreciated that the daily averaged current supplied to both the first DLG and the second DLG is generally increasing over time. By regularly determining an average of the first plurality of averaged values, e.g. the hourly average values, within a second time interval, e.g. a day, a second plurality of averaged values is produced.

FIG. 4c shows a 'daily average maximum' current plot. The daily average maximum is the daily average of all maximum hourly values recorded. First, a maximum current value within every hour the machine is in operation is recorded. Then, the daily average maximum is determined, or calculated, by averaging over each of these 'hourly maximum' values in a day. The plot shown in FIG. 4c shows the daily maximum current value over a period of approximately three months. Again, the graph shows a Y1 plot and a Y2 plot. The Y1 plot shown in FIG. 4c therefore shows the average of each of the maximum hourly currents supplied to the Y1 motor during each day the radiotherapy device was in operation. Producing the data for plot 4c can be described as producing a plurality of second time interval maximum values by regularly determining the maximum received signal within the first time interval (e.g. the hourly maximum values), and regularly averaging over these maximum received signals during the second time interval (e.g. daily).

In a disclosed method, it is possible to determine whether repair or replacement of the multi-leaf collimator should be scheduled. As set out above, the multi-leaf collimator comprises a leaf bank comprising a plurality of leaves, a leaf bank support configured to support the leaf bank, a leaf bank guide, and a guide motor configured to both extend the leaf bank along the leaf bank guide into the path of a radiation beam and withdraw the leaf bank from the path of a radiation beam along the leaf bank guide. The bank guide may be described as a linear slide upon which the leaf bank support is driven.

Reference is now made to the method depicted in the flowchart of FIG. 5. At step 510, a signal indicative of current supplied to the guide actuation means (guide motor) is received, for example at the device controller 240, remote controller 260 or central controller 270. The signals are processed 520 and, based on the processing, it is determined 530 whether repair or replacement of the multi-leaf collimator should be scheduled. In this case, the processing comprises regularly determining an average of the received current signals within a first time interval to produce a plurality of first averaged values. In some implementations, the first time interval is an hour, such that an average current value is determined for each hour in which signals are received from the current sensing means. A plot of this regular determination of an hourly average is shown in FIG. 4b. Current values/signals associated with times when the radiotherapy machine was not in operation are excluded from the averages.

The processing 520 further comprises regularly determining an average of the received signals over a second time interval to produce a plurality of second averaged values. The second time interval is longer than the first time interval. In one implementation, the second time interval is a day, such that the regularly determined second averaged values each comprise a 'daily average', or the average hourly current for every day in which signals are received from the current sensing means. These calculations are regularly performed such that it is possible to plot the first averages values in the manner depicted in FIG. 4b, and the second averages values in the manner depicted in FIG. 4a.

In an implementation, the average current value received for every hour is determined, such that each hour the machine is in operation is associated with a respective average value. These form the first averaged values.

Then, all these average values in a particular day are averaged so as to obtain a daily average. A collection of daily averages forms the second averaged values.

The processing further comprises determining whether the first averaged values meet a first threshold criterion, and determining whether the second averaged values meet a second threshold criterion. This may comprise monitoring the determined first averaged values to identify if the first threshold criterion is met, and monitoring the determined second averaged values to identify if the second threshold criterion is met.

In an example, the first threshold criterion is that the first averaged values have increased by more than a first threshold amount or percentage within a monitoring time period. It has been noted that an increasing spike on the 'All Means' chart shown in FIG. 4b is indicative that the MLC, and more specifically the DLG of the MLC, may need to be repaired or replaced. Identifying an increasing spike can be quantified as determining that the average hourly current supplied to the actuation means has increased by more than 10% or 30% in a monitoring period. Other ways of identifying a statistically significant increase will be known to the skilled person. A suitable monitoring period is a week.

In this example, the second threshold criterion is that the second averaged values have increased by more than a second threshold amount or percentage within a monitoring time period. The first and second threshold amounts and percentages may be equal. It has been noted that an increase in Y1 current in the 'Daily Mean' chart shown in FIG. 4a is indicative that the MLC, and more specifically the DLG of the MLC, may need to be repaired or replaced. This can be quantified as determining that the daily average current supplied to the actuation means has increased by more than 10% or 30% in a monitoring period. Other ways of identifying a statistically significant increase will be known to the skilled person. A suitable monitoring period is a week.

By averaging the data over two different time periods, the data is processed at different levels of granularity and the determination that the MLC should be repaired or replaced reaches a greater level of certainty.

The processing 520 may further comprise producing a plurality of second time interval maximum values by regularly determining a maximum of the received signals within the first time interval, e.g. an hour to produce hourly maximum values, and then averaging over each of the resulting values which fall within a second, longer time interval, e.g. a day to produce daily maximum values. For example, these maximum values may be produced to allow a plot such as that shown in FIG. 4c to be produced. The processing may further comprise determining whether the second time interval maximum values meet a third threshold criterion, such as whether the second time interval maximum values have increased by more than a third threshold percentage within the monitoring time period. In an example, the third threshold criteria may additionally comprise determining whether the regularly determined second time interval maximum values have exceeded a threshold amount.

By monitoring averaged current values while also monitoring maximum current values within a particular time interval and comparing each of these to threshold criteria, a greater certainty that the MLC should be repaired or replaced can be achieved.

At step 530, it is determined, based on the processing, that the MLC should be scheduled for repair or replacement. This comprises determining whether the first and second threshold criteria are met and, if they are, determining that a repair or replacement should be scheduled. This also may comprise determining whether one or more of the other criteria described above are met. If they are, it is determined that the MLC should be scheduled for repair or replacement.

Optionally, the processing may comprise outputting the determination at step 540. Outputting the determination may comprise displaying an indication of the determination on a display screen. It may comprise issuing an alert detailing the determination to a field service engineer. Such an alert may be delivered to the personal electronic device of the field service engineer, along with guides and workflows detailing how to perform the repair or replacement. Outputting the determination may comprise automatically issuing a notification to the owner of the radiotherapy device to schedule the repair or replacement. Again, this notification may include information regarding the detected fault along with guides and workflows detailing how to perform the repair or replacement.

In some implementations, the processing may comprise additional steps which either increase the certainty that the MLC is at fault, or else which allow a differentiation of which component of the MLC requires maintenance. Example MLC components which may cause a fault include the drive PCB, the brakes of the MLC system.

By monitoring the currents supplied to both the Y1 and the Y2 sides of the MLC, it is possible to identify that an MLC fault is associated with a leaf bank guide and/or a guide brake on a particular side (Y1 or Y2) of the MLC. IT is also possible to diagnose that a problem is associated with a component that affects both the Y1 and the Y2 side of the MLC equally, such as the control means e.g. a drive PCB. By monitoring both the Y1 and Y2 currents, producing first and second sets of averaged values for both 'sides' of the MLC, and comparing each of the resulting pluralities of averaged values to the various threshold criteria described above, it is possible to identify that, for example, the first and second threshold criteria are met for the Y1 components but not for the Y2 components. In this case, it is likely that the fault is associated with the Y1 guide brake or the Y1 leaf bank guide. For example, the Y1 leaf bank guide may require lubrication and/or the guide brake.

For completeness, it should be noted that to perform these additional, optional diagnostic steps, the radiotherapy device should comprise a Y1 and a Y2 leaf bank each comprising a respective plurality of leaves, a Y1 and a Y2 leaf bank guide, and both a Y1 and a Y2 guide actuation means. As the Y1 leaf bank support is configured to support the Y1 leaf bank, the Y2 leaf bank support is configured to support the Y2 leaf bank. The Y2 guide actuations means is configured to extend the Y2 leaf bank along the Y2 leaf bank guide into the path of a radiation beam. The device may also comprise both a Y1 guide brake configured to halt the movement of the first leaf bank, and a Y2 guide brake configured to halt the movement of the second leaf bank. The current sensing means is additionally configured to produce a signal indicative of the current supplied to the Y2 guide actuation means. The radiotherapy device may further comprise control means for controlling the first and the second guide actuation means, which may additionally also control the guide brakes.

The method then additionally comprises receiving at 510 a first set of signals from the current sensing means indicative of current supplied to the first (Y1) guide actuation means, and receiving a second set of signals from the current sensing means indicative of current supplied to the second (Y2) guide actuation means. At 520, the processing of the signals additionally comprises producing a plurality of first averaged values for both the first and the second set of signals by regularly determining an average of the received signals within the first time interval, and producing a plurality of second averaged values for both the first and the second set of signals by regularly determining an average of the received signals within the second time interval. It is then determined whether the first averaged values for either the first and the second set of signals meet the first threshold criterion. It is also determined whether the second averaged values for either the first and the second set of signals meet the second threshold criterion. Optionally, the maximum currents can be received and processed from both the Y1 and the Y2 guide actuation means as described in relation to just the Y1 guide actuation means above.

For cases in which signals indicative of current supplied to the first (Y1) guide actuation means meet the criteria, but signals indicative of current supplied to the second (Y1) guide actuation means do not meet the criteria, it can be determined that it is one of the Y1 components which must be repaired or replaced. In particular, one of the first (Y1) leaf bank guide and the first (Y1) guide brake should be repaired or replaced.

For cases in which signals indicative of current supplied to the first (Y1) guide actuation means and the second (Y2) guide actuation means meet the criteria, it is determined that repair or replacement of the control means, which may be a drive PCB, should be repaired or replaced.

Position determining apparatus repair and replacement/ UV LED method In a disclosed method, it is possible to determine whether repair or replacement of the position determining apparatus of the radiotherapy device should be scheduled. With reference to the flowchart of FIG. 5, signals are received 510, for example at the device controller 240, remote controller 260 or central controller 270. These signals comprise both signals indicative of current supplied to the source of illumination 603 and signals indicative of temperature at the source of illumination 603. These signals are received from a current sensing means 230 and a temperature sensing means 230 which are configured and suitably positioned in order to produce and provide these signals.

The method generally comprises processing these signals 520, and then, based on the processing, determining 530 that repair or replacement of a component of a radiotherapy device should be scheduled.

Processing 520 the received values comprises determining whether the signal indicative of current supplied to the source of illumination is above a current threshold. In an implementation, this determination is carried out on a regular basis, which may be described as monitoring the current signals to determine whether the current threshold has been exceeded.

Processing 520 the received values also comprises determining whether the signal indicative of temperature at the source of illumination is above a temperature threshold. In an implementation, this determination is carried out on a regular basis, which may be described as monitoring the temperature signals to determine whether the temperature threshold has been exceeded.

At step 530, it is determined, based on the processing, whether repair or replacement of the position determining device should be scheduled. The determination is made and the repair or replacement may be scheduled if both the current and temperature signals meet the thresholds. In particular, it is determined that the source of illumination must be replaced or repaired.

At step 540, the determination may be outputted in a manner described elsewhere herein with respect other disclosed methods.

In an example, similar to the methods described elsewhere herein, the processing may further comprise producing a plurality of first averaged values by regularly determining an average of the received signals within a first time interval, for example an hour. This can be done for both the current and the temperature signals. The first time interval may be an hour such that hourly average temperature and current values are determined. In an implementation, it is these hourly average values which are compared to the current or temperature thresholds described above.

In an example, similar to the methods described elsewhere herein, the processing may further comprise producing a plurality of second averaged values by regularly determining an average of the received signals within a second time interval. The second time interval may be a day, such that the second averaged values may be described as daily averages. In an implementation, it is these daily average values which are compared to the current or temperature thresholds described above.

Predictive Diaphragm Data and Method

In a disclosed method, it is possible to determine whether repair or replacement of the diaphragm apparatus for a radiotherapy device should be scheduled. The diaphragm apparatus comprises a diaphragm 214 and diaphragm actuation means configured to extend the diaphragm into the path of a radiation beam. The device further comprises current sensing means configured to produce a signal indicative of the current supplied to the diaphragm actuation means.

With reference to the flowchart of FIG. 5, signals are received 510, for example at the device controller 240, remote controller 260 or central controller 270. These signals comprise signals indicative of current supplied to the diaphragm actuation means.

The method comprises processing these signals 520. FIGS. 7a-c show signals which have been received and processed. FIG. 7a bears similarity to FIG. 4a and the skilled person will appreciate that the description of the data depicted in FIG. 4a is at least partly applicable to the data depicted in FIG. 7a. Similarly, FIGS. 7b and 7c bear similarity to FIGS. 4b and 4c respectively and the skilled person will appreciate that the description of the data depicted in FIGS. 4b and 4c is at least partly applicable to the data depicted in FIGS. 7b and 7c.

FIG. 7b shows the all means, or hourly average, plot. The graph shows current values averaged over successive hours for every hour the machine is in operation. In other words, each plotted point on the 'all means' graph is an averaged current value formed by averaging the current values connected with a particular diaphragm received in a particular hour. The X1 hourly mean plot is denoted in blue and is generally below the X2 hourly mean current, shown in red. By regularly determining an average of the received X1 (or X2) current signals within a second time interval, i.e. an hour, a second plurality of averaged values is produced. X1 refers to signals and values received in relation to a first diaphragm of the diaphragm apparatus, and X2 refers to signals and values received in relation to a second diaphragm of the diaphragm apparatus. By regularly determining an average of the received X1 (or X2) current signals within a first time interval, e.g. an hour, a first plurality of averaged values is produced. This first plurality of averaged values can be described as hourly averaged values.

FIG. 7a shows the daily mean current plot. The daily mean is the average of each hourly average value within a particular day. The X1 mean current is denoted in blue and it will be appreciated that the X1 current line of the particular machine in question is below the X2 current line. The daily mean plot is made up of data points from every day the radiotherapy device is in operation. The daily X1 mean for a particular day can be thought of as the average current value supplied to the first diaphragm during that day. The X2 daily mean value is calculated in a similar manner, i.e. by averaging the determined hourly X2 current values provided over a particular day. By regularly determining an average of the first averaged values within a second time interval, e.g. a day, a plurality of second averaged values may be produced. These second averaged values are plotted in FIG. 7a.

FIG. 7c shows a 'daily average maximum' current plot. The daily average maximum is the daily average of all maximum hourly values recorded. First, a maximum current value within every hour the machine is in operation is recorded. Then, the daily average maximums are determined, or calculated, by averaging over each of these 'hourly maximum' values each day. The plot shown in FIG. 4c shows the daily maximum current value over a period of approximately three months. The graph shows an X1 plot in blue which is generally above the X2 plot in red during the first half of the graph, before the red X2 daily average maximum current increases to above the blue X1 line in the second half of the graph. The plot shown in FIG. 7c therefore shows the average of each of the maximum hourly currents supplied to the X1 motor during each day the radiotherapy device was in operation.

Returning to discussion of FIG. 5, at step 530, based on the processing, it is determined whether repair or replacement of a diaphragm apparatus of a radiotherapy device should be scheduled. Optionally, the determination is then outputted 540 in a manner similar or identical to that described elsewhere herein for other disclosed methods.

Processing at step 520 comprises producing a plurality of averaged values by regularly determining an average of the received signals within a first time interval. The first time interval may be an hour, such that the plurality of averaged values comprises a plurality of hourly mean values such as those plotted in FIG. 7b. Processing at step 520 also comprises producing a plurality of daily average maximum values by regularly determining a maximum received signal within the first time interval and averaging over these maximum received signals over the second time interval An example plurality of daily average maximum values is plotted in FIG. 7c.

In more detail regarding the daily average maximum values, or more generally the second time interval maximum values, these values may be produced by producing a plurality of first time interval maximum values by regularly determining a maximum received signal within the first time interval (e.g. by determining the maximum received value within an hour), then producing a plurality of second time interval maximum values based on the first time interval maximum values. This is done by regularly averaging the determined first time interval maximum values within, or over, the second time interval. Therefore, in an implementation in which the first time interval is an hour and the second time interval is a day, processing the signals comprises regularly determining an hourly average value from the received signals, regularly determining a daily average value from the hourly average values, determining whether the hourly average values meet a first threshold criterion, and determining whether the daily average values meet a second threshold criterion.

The processing further comprises determining whether the averaged values meet a first threshold criterion and determining whether the second time interval maximum values meet a second threshold criterion. Determining whether the averaged values meet a first threshold criterion may comprises determining whether the averaged values have increased by a first threshold amount within a second time interval, for example in a week. The threshold amount might be a threshold percentage amount, such as 30%. In an implementation, the processing involves monitoring the values/signals depicted in FIG. 7b to determine whether the values have increased by more than 30% in the last week.

Similarly, determining whether the second time interval maximum values meet a second threshold criterion may comprise determining whether the values have increased by a second threshold amount within the second time interval. Again, this may be a threshold percentage amount such as 30%. In an implementation, the processing involves monitoring the values/signals depicted in FIG. 7c to determine whether the values have increased by more than 30% in the last week.

Reference is made herein to the daily average of a data item, or the daily maximum of a data item. In a preferred implementation, these values are determined by regularly averaging over each of the hourly mean, or hourly maximum, values in a day. However, it will be appreciated that a daily average can alternatively be determined by averaging over all received values within a day, and a daily maximum can be determined by determining the maximum received value within a day.

Methods of the present disclosure may be described as computer-implemented methods which allow a determination that a component of a radiotherapy device, for example a MLC leaf position determination system and/or an MLC in a clinical linac device, should be scheduled for repair or replacement. Repair of these devices may comprise replacing them. The present techniques therefore describe cost-effective, efficient and predictive methods of preventing a fault. It has to date proved impossible to determine the condition of in-service components in order to predict when maintenance should be performed. The present approach provides cost and time savings over the prior methods because servicing and maintenance in the form of repair and replacement of the described components is only performed when needed, and downtime of the device is reduced due to reducing or eliminating entirely the number of safety interrupts usually associated with degrading component performance, and also by eliminating time spent diagnosing the problem before repair is effected.

Clauses—A Method of Determining Whether Repair or Replacement of a Source of Illumination in a Position Determining Apparatus should be Scheduled—UV LED 1. A computer-implemented method of determining whether repair or replacement of a position determining apparatus should be scheduled, the position determining apparatus being configured to determine the position of one or more leaves of a multi-leaf collimator for a radiotherapy device, each of the one or more leaves comprising an optical marker, the position determining apparatus comprising a source of illumination configured to illuminate the one or more leaves and a light detection means configured to detect light from the optical markers;

the position determining device further comprising current sensing means configured to produce a signal indicative of current supplied to the source of illumination and temperature sensing means configured to produce a signal indicative of temperature at the source of illumination;

wherein the method comprises:
receiving a signal indicative of current supplied to the source of illumination;
receiving a signal indicative of temperature at the source of illumination;
processing the received signals; and
based on the processing, determining whether repair or replacement of the position determining apparatus should be scheduled.

Optionally, processing the received values may comprise:
determining whether the signal indicative of current supplied to the source of illumination is above a current threshold; and
determining whether the signal indicative of temperature at the source of illumination is above a temperature threshold.

2. The method of clause 1, wherein the source of illumination comprises an LED.
3. The method of any preceding clause, wherein the source of illumination is configured to emit UV light.
4. The method of any preceding clause, wherein the optical markers are configured and positioned to receive light emitted by the source of illumination, and re-emit the light by a process of reflection or fluorescence.
5. The method of any preceding clause, wherein the light detection means is configured to produce a signal indicative of the light received by the light detection means to a control means, the control means being configured to:
monitor signals received from the light detection means; and,
control the current supplied to the source of illumination based on the received signals from the light detection means.
6. The method of clause 5, wherein controlling the current supplied to the source of illumination comprises increasing the current supplied to the source of illumination based on a determination that the received signals from the light detection means have fallen below a threshold value.
7. The method of any preceding clause, further comprising outputting the determination of whether repair or replacement of the source of illumination should be scheduled.

The method of clause 7, wherein outputting the determination comprises at least one of displaying an indication of the determination on a display screen; issuing an alert detailing the determination to a field service engineer; and/or automatically issuing a notification to the owner of the radiotherapy device to schedule the repair or replacement.

A computer-readable medium comprising computer-executable instructions which, when executed by a processor, cause the processor to perform the method of any preceding clause.

8. A system comprising a remote controller communicatively coupled to a central controller via a network, the central controller configured to receive signals produced by a current sensing means and a temperature sensing means of a radiotherapy device comprising a position determining apparatus, the position determining apparatus being configured to determine the position of one or more leaves of a multi-leaf collimator of the radiotherapy device, each of the one or more leaves comprising an optical marker, the position determining apparatus comprising a source of illumination configured to illuminate the one or more leaves and a light detection means configured to detect light from the optical markers; the current sensing means configured to produce a signal indicative of current supplied to the source of illumination and the temperature sensing means configured to produce a signal indicative of temperature at the source of illumination, the remote controller further being configured to:
request, from the central controller, signals received from the current sensing means and the temperature sensing means; and
perform the method of any of clauses 1 to 8.

Clauses—A Method of Determining Whether Repair or Replacement of a Diaphragm Apparatus should be Scheduled—Predictive Diaphragm 1. A computer-implemented method of determining whether repair or replacement of a diaphragm apparatus for a radiotherapy device should be scheduled, the diaphragm apparatus comprising a diaphragm and diaphragm actuation means configured to extend the diaphragm into the path of a radiation beam; the device further comprising current sensing means configured to produce a signal indicative of the current supplied to the diaphragm actuation means;
the method comprising:
receiving signals from the current sensing means;
processing the signals; and
based on the processing, determining whether repair or replacement of the diaphragm apparatus should be scheduled.
2. The method of clause 1, wherein the processing comprises:
producing a plurality of averaged values by regularly determining an average of the received signals within a first time interval; and
determining whether the averaged values meet a first threshold criterion.
3. The method of clause 1 or clause 2, wherein the processing further comprises:
producing a plurality of first time interval maximum values by regularly determining a maximum received signal within the first time interval,
producing a plurality of second time interval maximum values based on the first time interval maximum values, and
determining whether the second time interval maximum values meet a second threshold criterion.
4. The method of clause 3, wherein producing a plurality of second time interval maximum values based on the first time interval maximum values comprises regularly averaging the determined first time interval maximum values within the second time interval.
5. The method of any of clauses 2 to 4, wherein the first time interval is an hour.
6. The method of any of clauses 3 to 6, wherein the second time interval is a day.
7. The method of any preceding clause, wherein processing the signals comprises regularly determining an hourly average value from the received signals, regularly determining a daily average value from the hourly average values, determining whether the hourly average values meet a first threshold criterion, and determining whether the daily average values meet a second threshold criterion.
8. The method of any of clauses 2 to 7, wherein determining whether the averaged values meet a first threshold criterion comprises determining whether the averaged values have increased by a first threshold amount within a monitoring time period.

9. The method of any of clauses 3 to 8, wherein determining whether the second time interval maximum values meet a second threshold criterion comprises determining whether the second time interval maximum values have increased by a second threshold amount within a second time interval.

10. The method of clause 8 or clause 9, wherein the first and/or the second threshold amount is a threshold percentage increase.

11. The method of any preceding clause, further comprising outputting the determination of whether repair or replacement of the position determining apparatus should be scheduled.

12. The method of clause 11, wherein outputting the determination comprises at least one of displaying an indication of the determination on a display screen; issuing an alert detailing the determination to a field service engineer; and/or automatically issuing a notification to the owner of the radiotherapy device to schedule the repair or replacement.

13. A computer-readable medium comprising computer-executable instructions which, when executed by a processor, cause the processor to perform the method of any preceding clause.

14. A system comprising a remote controller communicatively coupled to a central controller via a network, the central controller configured to receive signals produced by a current sensing means of a radiotherapy device comprising a diaphragm apparatus, the diaphragm apparatus comprising a diaphragm and diaphragm actuation means configured to extend the diaphragm into the path of a radiation beam; the current sensing means being configured to produce a signal indicative of the current supplied to the diaphragm actuation means, the remote controller further being configured to:
request, from the central controller, signals received from the current sensing means; and
perform the method of any of clauses 1 to 12.

The above implementations have been described by way of example only, and the described implementations and arrangements are to be considered in all respects only as illustrative and not restrictive. It will be appreciated that variations of the described implementations and arrangements may be made without departing from the scope of the invention.

The invention claimed is:

1. A computer-implemented method of determining whether repair or replacement of a beam limiting device for a radiotherapy device should be scheduled, the beam limiting device comprising:
at least one beam limiting component;
a guide actuation member configured to extend the at least one beam limiting component into a path of a radiation beam; and
a current sensor configured to produce a signal indicative of the current supplied to the guide actuation member;
the method comprising:
receiving one or more signals from the current sensor;
processing the one or more signals; and
based on the processing, determining whether repair or replacement of the beam limiting device should be scheduled, wherein the processing comprises:
producing a plurality of first averaged values by recurrently determining an average of the received one or more signals within a first time interval; and
determining whether the first averaged values meet a first threshold criterion.

2. The method of claim 1, wherein the processing comprises:
producing a plurality of second averaged values by recurrently determining an average of the first averaged values within a second time interval; and
determining whether the second averaged values meet a second threshold criterion.

3. The method of claim 2, further comprising:
determining that repair or replacement of the beam limiting device should be scheduled when it is determined that each of the first threshold criterion and the second threshold criterion are met.

4. The method of claim 2, wherein the first time interval is shorter than the second time interval.

5. The method of claim 2, wherein the second time interval is a day, and the second averaged values are daily averages of the first averaged values.

6. The method of claim 2, wherein the second threshold criterion is that that the second averaged values have increased by more than a second threshold percentage within a monitoring time period.

7. The method of claim 2, wherein the beam limiting device is a multi-leaf collimator and the at least one beam limiting component is a first leaf bank comprising two or more of leaves, the multi-leaf collimator further comprising:
a first leaf bank support configured to support the leaf bank,
a first leaf bank guide, wherein the guide actuation member is a first guide actuation member configured to extend the leaf bank along the leaf bank guide into the path of the radiation beam; and
a second leaf bank comprising two or more leaves, a second leaf bank support configured to support the second leaf bank, a second leaf bank guide, and a second guide actuation member configured to extend the second leaf bank along the second leaf bank guide into the path of a radiation beam;
wherein the current sensor is further configured to produce a signal indicative of the current supplied to the second guide actuation member; wherein the method further comprises:
receiving a first set of signals from the current sensor indicative of current supplied to the first guide actuation member; and
receiving a second set of signals from the current sensor indicative of current supplied to the second guide actuation member;
and wherein processing the signals comprises:
producing a plurality of first averaged values for both the first and the second set of signals by recurrently determining an average of the received signals within the first time interval;
producing a plurality of second averaged values for both the first and the second set of signals by recurrently determining an average of the first averaged values within the second time interval;
determining whether the first averaged values for either the first and the second set of signals meet a first threshold criterion; and determining whether the second averaged values for either the first and the second set of signals meet a second threshold criterion.

8. The method of claim 7, wherein the device further comprises:
a first guide brake configured to halt movement of the first leaf bank; and
a second guide brake configured to halt movement of the second leaf bank; wherein determining that repair or replacement of the multi-leaf collimator should be scheduled, based on the processing, comprises:
upon a determination that each of the first threshold criterion and the second threshold criterion are met for the first set of signals but not for the second set of signals, determining that one or both of the first leaf bank guide and the first guide brake should be repaired or replaced.

9. The method of claim 7, wherein the radiotherapy device further comprises:
a controller for controlling the first and the second guide actuation member, and wherein determining that repair or replacement of the multi-leaf collimator should be scheduled, based on the processing, comprises:
upon a determination that each of the first threshold criterion and the second threshold criterion are met for both the first set of signals and the second set of signals, determining that the controller should be repaired or replaced.

10. The method of claim 1, wherein the first time interval is an hour, and the first averaged values are hourly averages.

11. The method of claim 1, wherein the first threshold criterion is that the first averaged values have increased by more than a first threshold percentage within a monitoring time period.

12. The method of claim 1, wherein the processing further comprises:
producing two or more first time interval maximum values by recurrently determining a maximum received signal within the first time interval;
producing two or more second time interval maximum values based on the first time interval maximum values; and
determining whether the second time interval maximum values meet a third threshold criterion.

13. The method of claim 12, wherein producing the two or more second time interval maximum values based on the first time interval maximum values comprises recurrently averaging the determined first time interval maximum values within the second time interval.

14. The method of claim 10, wherein the third threshold criterion is that the second time interval maximum values have increased by more than a third threshold percentage within a monitoring time period.

15. The method of claim 1, wherein the at least one beam limiting component comprises at least one of:
a leaf bank of a multi-leaf collimator, wherein the leaf bank comprises two or more leaves; and
a diaphragm.

16. The method of claim 1, further comprising:
outputting the determination.

17. The method of claim 16, wherein outputting the determination comprises at least one of displaying an indication of the determination on a display screen, issuing an alert detailing the determination to a field service engineer, or automatically issuing a notification to an owner of the radiotherapy device to schedule the repair or replacement.

18. A non-transitory computer-readable medium comprising computer-executable instructions which, when executed by a processor, cause the processor to perform a method of determining whether repair or replacement of a beam limiting device for a radiotherapy device should be scheduled, the beam limiting device comprising at least one beam limiting component and actuation means configured to extend the at least one beam limiting component into a path of a radiation beam; the device further comprising current sensing means configured to produce a signal indicative of the current supplied to the actuation means; the method comprising:
receiving a signal from the current sensing means;
processing the signal received from the current sensing means; and
based on the processing, determining whether repair or replacement of the beam limiting device should be schedule, wherein the processing comprises:
producing a plurality of first averaged values by recurrently determining an average of the received one or more signals within a first time interval; and
determining whether the first averaged values meet a first threshold criterion.

19. A system comprising:
a remote controller communicatively coupled to a central controller via a network, the central controller configured to receive signals produced by a current sensor of a radiotherapy device, the radiotherapy device comprising:
a beam limiting device, the beam limiting device comprising at least one beam limiting component; and
an actuation member configured to extend the at least one beam limiting component into a path of a radiation beam, wherein the current sensor configured to produce a signal indicative of the current supplied to the actuation member, and wherein the remote controller further being configured to:
request, from the central controller, one or more signals received from the current sensor;
receive the one or more signals from the current sensor;
process the one or more signals received from the current sensor; and
based on the processing, determine whether repair or replacement of the beam limiting device should be scheduled, wherein the processing comprises:
producing a plurality of first averaged values by recurrently determining an average of the received one or more signals within a first time interval; and
determining whether the first averaged values meet a first threshold criterion.

* * * * *